United States Patent [19]

Galindo

[11] Patent Number: 4,519,793
[45] Date of Patent: May 28, 1985

[54] CATHETER HOLDER

[76] Inventor: Eugene R. Galindo, 2926 Highridge Rd., La Cresenta, Calif. 91214

[21] Appl. No.: 465,302

[22] Filed: Feb. 9, 1983

[51] Int. Cl.³ ............................................. A61M 25/02
[52] U.S. Cl. .................................. 604/180; 604/326; 128/DIG. 26; 285/4
[58] Field of Search ................ 604/180, 174, 326; 128/DIG. 26; 141/331, 337, 382; 285/3, 4, 177; 222/541

[56] References Cited

U.S. PATENT DOCUMENTS

| | | | |
|---|---|---|---|
| 2,981,449 | 4/1961 | Perkins | 222/541 |
| 3,487,837 | 1/1970 | Peterson | 604/180 |
| 3,683,911 | 8/1972 | McCormick | 604/180 |
| 4,069,826 | 1/1978 | Sessions et al. | 604/175 |
| 4,120,129 | 10/1978 | Nagler et al. | 285/4 |

*Primary Examiner*—Stephen C. Pellegrino
*Attorney, Agent, or Firm*—Cislo, O'Reilly & Thomas

[57] ABSTRACT

A catheter holder system particularly useful for the stabilization of medical tubes and the like, particularly useful for association with ostomy receptacles. The catheter holder comprises a molded, conformable plastic member much in the configuration of a funnel or the like having a planar, annular or base portion wherein the member is of semi-rigid, upstanding construction whereby the extreme terminus of the funnel portion terminates in a tip portion which is easily separable in order to accommodate and receive various size medical tubing therethrough in order to maintain the tubing in a secure and stable position relative to the patient with which the tubing is utilized. In most instances the tubing will comprise a catheter which may be passed through the funnel portion of the member and snugly retained by friction fit therein. The catheter holder is easily adapted into a system comprising the holder member and an ostomy bag and to facilitate the assemblage, the catheter holder, or more specifically, the undersurface of the base thereof, is provided with an adhesive layer protected by a peelable sheet.

6 Claims, 5 Drawing Figures

CATHETER HOLDER

BACKGROUND OF THE INVENTION

In many instances of modern day medicine, it becomes necessary to have various medical tubing or the like placed within the human body for excretive purposes, drainage purposes and other uses. When, for example, a catheter or other medical tubing is placed within the body, it becomes desirable to be able to stabilize the medical tubes and to provide a contiguous area to the tubes which will be maintained in a hygenic manner.

Heretofore the medical profession has not had available to it a means of insuring that an in-placed catheter, medical tube, drain or the like would be stabilized against inadvertent movement by reason of manipulating the patient as for changing of dressings, bedding, or the like. Additionally, where the tubing exits the body, it has been difficult to maintain that area in substantially germ-free or sanitary conditions because of the ambient and surrounding atmosphere or contiguous clothing, bedding and the like.

With the herein disclosed catheter holder system, it becomes possible to insure that a medical tube, whether it be a catheter or other device is stabilized in secure position to the patient's body and also provides a means of maintaining as clean and hygenic a condition surrounding the point where the tube exits the body as is possible. The catheter holder can ideally be used in a system comprising it and an ostomy bag or the like. The catheter holder, when used in conjunction with the ostomy bag provides a means of conveying the drainage from an in dwelling catheter through an ostomy pouch into another collector.

OBJECTS AND SUMMARY OF THE INVENTION

It is an object of the invention to provide a catheter holder member for use by itself or in conjunction with a medical device.

It is another object of the invention to provide a catheter or medical tube holder which is useful for stabilizing catheters and medical tubes and the like.

It is another important object of the invention to provide a catheter or medical tube holder wherein the same is of integral, conformable construction and is adapted to have one end thereof severed at a selectable point so as to receive therethrough medical tubing in a friction-fit relationship.

It is another still important further object of the invention to provide an integral medical tube holder or the like comprising an upper funnel-like portion with an intermediate conical-shaped portion terminating in an annular base wherein the upper funnel portion is adapted to be severed to provide selected diameter openings through which medical tubing may be placed.

It is another even further, more specific important object of the invention to provide a medical tube holder and the like which is readily adaptable with medical devices, such as ostomy bags or the like.

It is another even further, still more specific important object of the invention to provide a medical tube holder of conformable, semi-rigid plastic material wherein the holder may be utilized by itself for stabilizing medical tubes or may be associated into a medical device system and wherein the base of the holder is provided a protected, adhesive layer for easy association with the body of a patient with which medical tubing or the like is to be used, or alternately, for ease of association with a medical device such as an ostomy bag.

In an exemplary embodiment, the invention relates to a medical tube holder or the like, comprising an integral member having an upper, funnel-like portion having an enclosed tip adapted for removal from the remainder thereof and wherein an intermediate, conically-shaped portion terminates in a bottom annular portion. The medical tube holder is of thin-walled, moldable material, with the bottom annular portion having substantially planar surfaces and the bottom surface thereof being adapted for adhesive securement to a supporting surface which may or may not comprise a medical device such as an ostomy bag. When the medical tube holder is associated from a supporting surface such as an ostomy bag or device, it is associated in such a manner that tubing may be placed through the ostomy bag or device for ease of removal of effluent from the in dwelling catheter.

These and other objects of the invention will become more apparent from the hereinafter following commentary taken in conjunction with the drawings.

DESCRIPTION OF THE BEST EMBODIMENTS CONTEMPLATED

Figure 1:
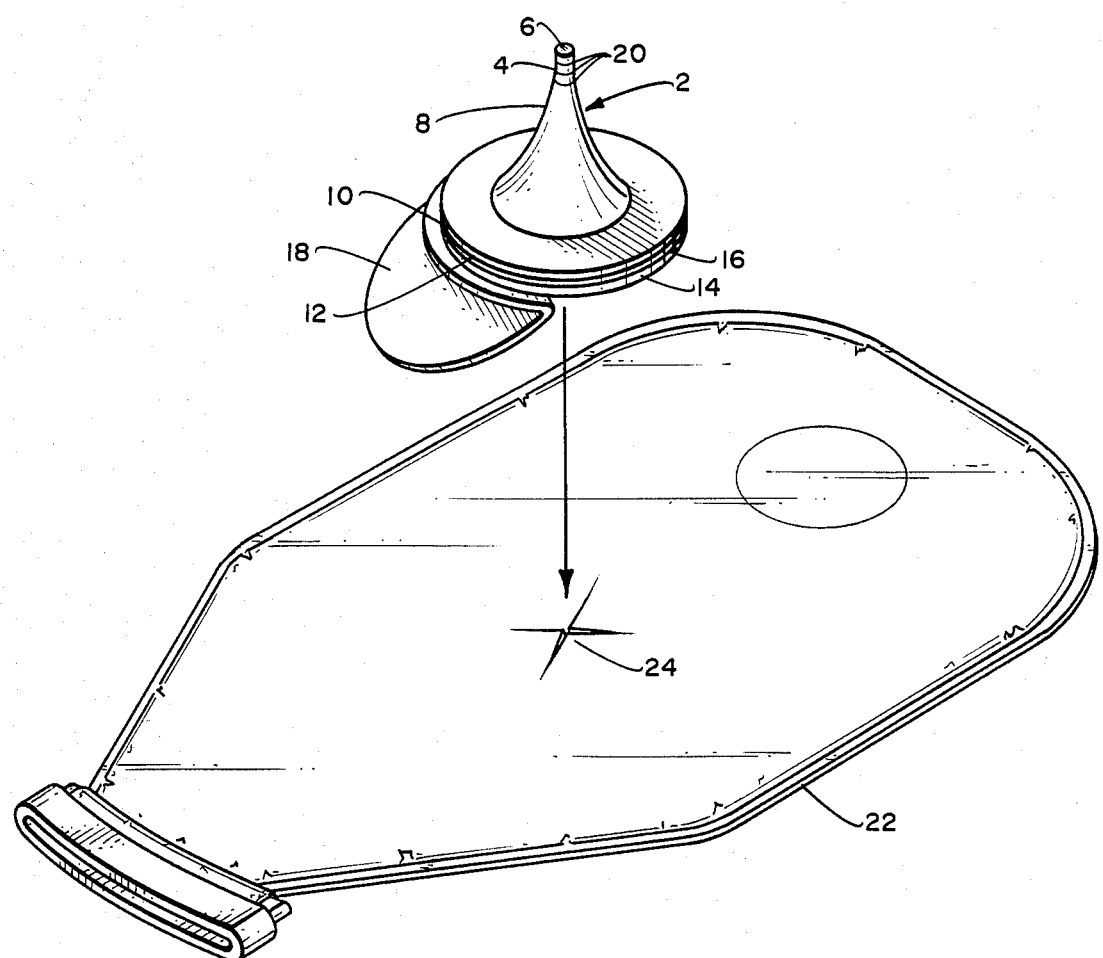
FIG. 1 is a perspective view of the medical tube holder of this invention, showing its positioning above a medical device such as an ostomy bag.
Figure 2:
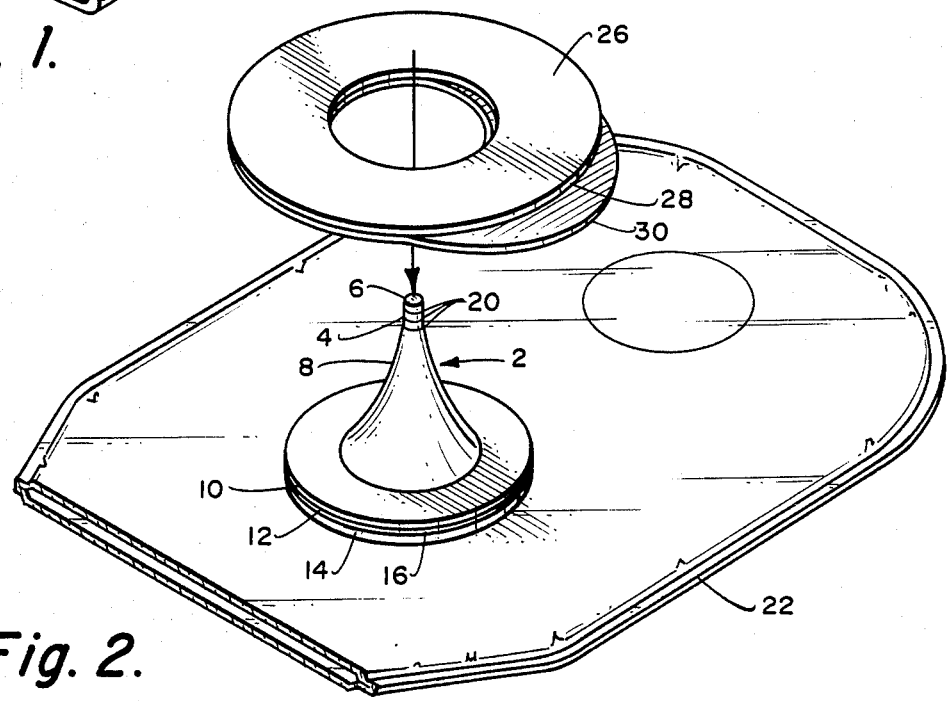
FIG. 2 is a perspective view illustrating placement of the catheter holder on an ostomy device or the like, and being readied to receive an annular member to insure liquid-proof securement of the holder to the ostomy bag.

Referring to the drawings wherein like numerals of reference will designate like elements throughout, it will be seen that the medical tube holder 2 comprises an integral member having an upper, tapering, funnel-like portion 4 terminating in a closed-end 6 and being interconnected to conically-shaped, intermediate portion 8 which terminates in substantially planar, annular portion 10 in this instance of thin-walled, plastic, conformable material, but of sufficient rigidity so as to maintain the portions 8 and 4 in the upright or freestanding positions as seen in FIG. 1 of the drawings.

The medical tube holder 2 has an undersurface 12 to which is secured a soft, conformable foam pad segment 14 to the undersurface of which is provided an adhesive layer 16 protected by peelable paper segment 18 as is conventional in the pressure sensitive adhesive art.

The thin layer of foam 14 is provided so as to be more easily accommodated by the skin of a human being or the like where the device is to be used to stabilize gastric tubes, for example, which are implanted into the stomach and through the abdominal wall. When the holder 2 of the invention is used by itself, removal of the paper layer 18 will provide ease of securement of the holder 2 to human skin and the like. Obviously, where the holder is used by itself, the closed-tip 6, or any portion of the elongated, funnel-like upper portion 4 is removed in order to thread the gastric tube or the like through the interior of the member 2. Placement of the member 2 in such manner provides substantial sealing of the area adjacent or contiguous the gastric tubes extending from the abdominal wall of the human being with which the holder 2 of the invention is utilized.

For most purposes, the holder 2 will be used for stabilization of gastric tubes, nephrostomy tubes, and any other type of catheter or tubing where stabilization and maintenance of sanitary, hygenic conditions in the contiguous areas are desirable.

However, the medical tube holder of the device will most practically find ubiquitous usage in conjunction with ostomy bags or other medical devices and which allows the use of an in dwelling catheter along with such devices. To facilitate removal of an upper portion of the funnel portion 4 of member 2, indicia lines such as 20, may be molded into the upper portion and marked off to indicate various diameter openings so as to facilitate threading or passage of medical tubing or catheters through the interior of device 2 as those of ordinary skill in the medical arts will well appreciate.

Referring now to more specific detail of the inventive system in conjunction with association of the medical tube holder 2 with an ostomy bag such as 22, it will be seen that the ostomy bag 22 is provided with an X-cut 24 being about 1–1¼ inches in size at a place in the ostomy bag 22 where it is desired to have a catheter protrude therefrom. The medical tube holder 2 is readied for positioning over the X-cut 24, the paper layer 18 is removed and the device 2 placed over the X-cut 24 and securely tamped down so as to insure the securement via the adhesive layer 16 of medical tube holder 2.

Figure 3:
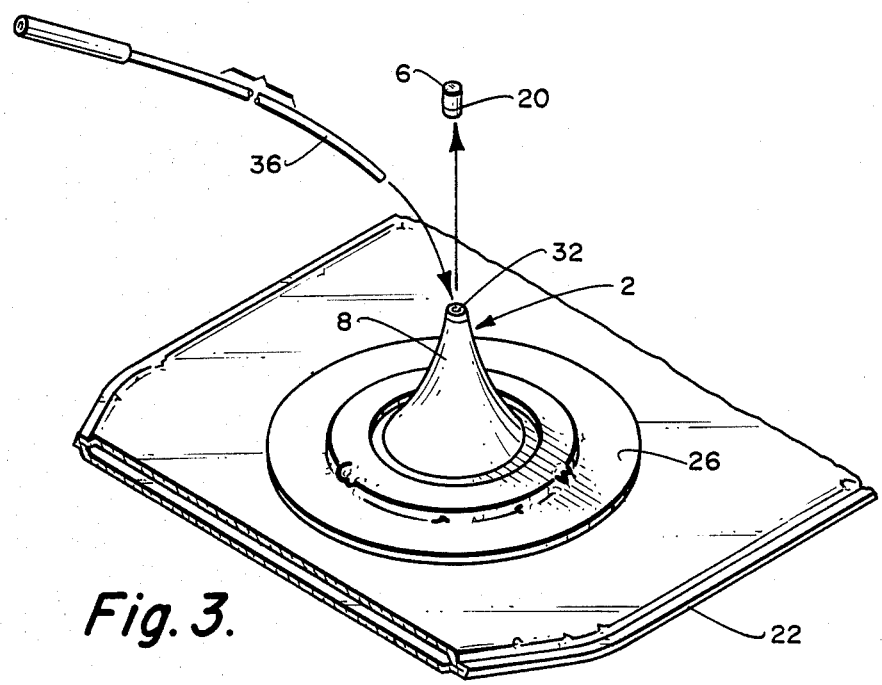
FIG. 3 illustrates the catheter holder in place and showing the removal of the closed-tip portion thereof and the threading of the medical tube or catheter through the aperture formed by the tip removal.
Figure 4:
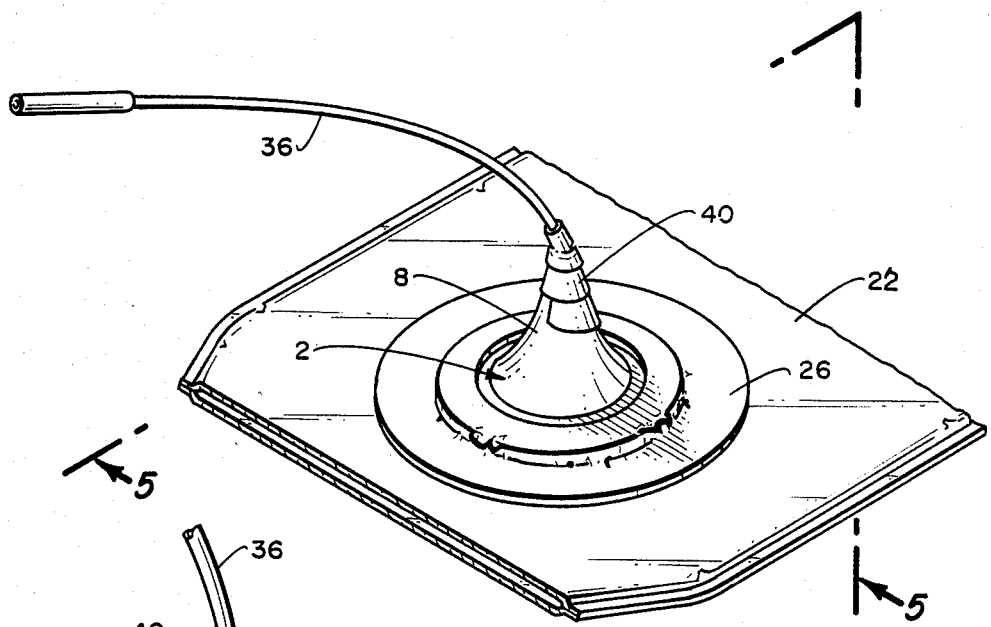
FIG. 4 illustrates the catheter or medical tube securement in the ostomy bag.
Figure 5:
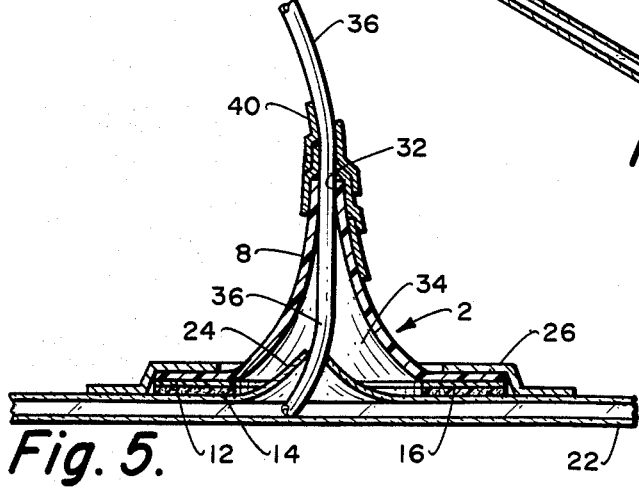
FIG. 5 is an enlarged view taken along the line 5—5 of FIG. 4.

Once in place over the X-cut 24, and in order to insure waterproof securement of the holder 2 to the ostomy receptacle 22, either strips of adhesive tape are placed about the annular flange portion 10 of member 2, or alternatively, and the preferred system, is to utilize an annular adhesive member 26 which has the under adhesive layer 28 protected by removable layer 30 and which is subsequently positioned as seen in FIG. 3.

Once the tube holder is in place, the upper tip portion 6 is removed, the cut being made along one of the selected indicia protuberances 20, which may be calibrated to indicate a particular diameter aperture such as 32 formed by the removal of the upper portion 6 from intermediate, conical portion 8.

The interior 34 of member 2 has positioned thereinto a medical tube such as 36 which is then threaded through the interior cavity 34 through the aperture 32 for securement into a satisfactory drainage facility for effluent that would be expected to drain from the in dwelling catheter or medical tube 36 in a manner well known in the art. In order to insure that the tubing 36 even though frictionally held in place through the aperture 32 remains in place, strips of adhesive 40 may be placed thereabout to insure proper securement of the tube 36 in the assemblage with the ostomy bag 22 and the catheter holder 2.

Thus, there has been disclosed a unique medical tube holder for association with medical tubes associated with the human body and used by itself in order to stabilize the medical tubes and to hold same in place and to provide a sanitary area adjacent where the tube exits the human body. The holder may be integrally molded of medical grade plastics or a latex.

While the invention has been described with respect to specific reference to specific details of construction, those of ordinary skill in the art will at once recognize that the medical tube holder, for example, need not be made of the specific, thin-wall type of conformable plastic material that has been illustrated, nor need it be made with an enclosed end portion adapted for severance, but instead may be fabricated in specific diameter end portions to receive specific diameter medical tubing. However, in order to have the greatest applicability and field of use the medical tube holder has been described and illustrated in the manner in which it has.

Those of ordinary skill in the art will at once recognize other modifications and changes that may be made to the herein described invention and all of which will not depart from the essence and spirit of the invention and all such changes and modifications are intended to be covered by the appended claims.

I claim:

1. A medical tube holder or the like comprising an integral member having an upper funnel-like portion, an intermediate, conically-shaped portion, and a bottom annular portion, said member being of thin-walled, moldable and conformable material, said bottom annular portion having substantially planar surfaces and the bottom surface thereof being adapted for adhesive securement to a supporting surface or the like, said funnel-like portion defining a substantially continuously tapered interior surface whereby said funnel-like portion is severable for accommodating differing diameter medical tubes or the like in frictional engagement therewith.

2. The medical tube holder of claim 1 wherein the upper, funnel-like portion has an enclosed tip adapted for removal from the remainder thereof.

3. The medical tube holder in accordance with claim 2 wherein said member is of elastomeric conformable material and is of semi-rigid construction such that the upper and intermediate portions are freestanding.

4. The medical tube holder in accordance with claim 3 which includes a foam layer on the undersurface of said planar surface in juxtaposition to said bottom annular portion and annular indicia about said upper funnel portion are provided to indicate lines of severance.

5. The medical tube holder in accordance with claim 4 wherein the undersurface of said cushion layer has a pressure sensitive adhesive layer with a peelable protecting layer secured to the exposed surface thereof.

6. The combination of an integral member medical tube holder or the like in association with a medical device comprising an ostomy receptacle wherein the medical tube holder has an upper funnel-like portion having an enclosed tip adapted for removal from the remainder thereof and an intermediate, conically-shaped portion terminating in a bottom annular portion, said integral member medical tube holder being of thin-walled, moldable plastic material and said bottom annular portion having substantially planar surfaces, the undersurface thereof being adapted for securement to an aperture in said ostomy receptacle by having an adhesive layer protected by a peelable sheet and including a medical tube extending from the interior of said ostomy receptacle through the interior of said integral member and providing a passageway through which effluent may flow.

* * * * *